United States Patent
Eisenbarth et al.

(10) Patent No.: US 9,939,448 B2
(45) Date of Patent: Apr. 10, 2018

(54) METHODS FOR DETECTING INSULIN AUTOANTIBODY

(75) Inventors: George S. Eisenbarth, Golden, CO (US); Liping Yu, Centennial, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 139 days.

(21) Appl. No.: 13/521,023

(22) PCT Filed: Jan. 6, 2011

(86) PCT No.: PCT/US2011/020300
§ 371 (c)(1),
(2), (4) Date: Jul. 31, 2012

(87) PCT Pub. No.: WO2011/085057
PCT Pub. Date: Jul. 14, 2011

(65) Prior Publication Data
US 2013/0011860 A1 Jan. 10, 2013

Related U.S. Application Data

(60) Provisional application No. 61/292,844, filed on Jan. 6, 2010.

(51) Int. Cl.
*G01N 33/68* (2006.01)
(52) U.S. Cl.
CPC ..... *G01N 33/6854* (2013.01); *G01N 2800/24* (2013.01)
(58) Field of Classification Search
CPC ............ G01N 33/6854; G01N 2800/24
See application file for complete search history.

(56) References Cited

U.S. PATENT DOCUMENTS

| 4,855,242 A | 8/1989 | Soeldner |
| 5,422,339 A * | 6/1995 | Eisenbarth ............ C07K 14/62 514/6.1 |
| 5,547,847 A | 8/1996 | Hagopian et al. |
| 7,001,775 B1 | 2/2006 | Burne et al. |
| 7,344,846 B2 | 3/2008 | Hageman et al. |
| 2006/0115860 A1 | 6/2006 | Cabrera et al. |

FOREIGN PATENT DOCUMENTS

WO    WO 9964447 A1 * 12/1999

OTHER PUBLICATIONS

Böhmer, et al., Proinsulin Autoantibodies are More Closely Associated with Type 1 (Insulin-Dependent) Diabetes Mellitus Than Insulin Autoantibodies. Diabetologia, 34(11): 830-834, 1991.*
Chen et al., Sensitive non-isotopic assays for autoantibodies to IA-2 and to a combination of both IA-2 and GAD65, Clinica Chimica Acta 357 (2005) 74-83.*
MSD, Meso Scale Discovery Clinical Immunology, 12 pages, 2007, retrieved from https://www.mesoscale.com/~/media/files/brochures/immunologybrochure.pdf on May 18, 2017.*
Liping Yu et al., "Distinguishing Persistent Insulin Autoantibodies With Differential Risk. Nonradioactive Bivalent Proinsulin/Insulin Autoantibody Assay," Diabetes, Jan. 2012, vol. 61, pp. 179-186.

* cited by examiner

*Primary Examiner* — Andrea S Grossman
(74) *Attorney, Agent, or Firm* — Saul Ewing Arnstein & Lehr LLP; Kathryn Doyle; Domingos J. Silva

(57) ABSTRACT

The present invention provides methods for detecting insulin autoantibody. Such methods can be used, for example, to predict susceptibility of and/or diagnose the presence of Type 1 diabetes in a subject. Some aspects of the invention also provide kits adapted for use in such methods. In particular, some aspects of the invention use proinsulin to detect the presence of insulin autoantibody.

2 Claims, 5 Drawing Sheets

METHODS FOR DETECTING INSULIN AUTOANTIBODY

CROSS-REFERENCE TO RELATED APPLICATIONS

This application claims the priority benefit of U.S. Provisional Application No. 61/292,844, filed Jan. 6, 2010, which is incorporated herein by reference in its entirety.

STATEMENT REGARDING FEDERALLY FUNDED RESEARCH

This invention was made with government support under grant number DK32083 and DERC grant DK 057516 awarded by the National Institutes of Health. The government has certain rights in the invention.

FIELD OF THE INVENTION

The present invention relates to methods for detecting insulin autoantibody and kits adapted for use in such methods.

BACKGROUND OF THE INVENTION

Insulin autoantibody are often the first autoantibody to appear prior to the development of Type 1A diabetes in children prospectively followed from birth. These autoantibody target one of four major islet autoantigens of autoantibody assays validated in CDC sponsored workshops of the Immunology of Diabetes Society (IDS). Early IDS workshops demonstrated that though multiple ELISA assays detected insulin antibodies following injection of subcutaneous insulin, standard ELISA formats were unable to detect insulin autoantibody of non-insulin treated new onset diabetic patients or individuals progressing to Type 1 diabetes. These standard ELISA assays bound insulin to solid substrates such as ELISA plates and attempted to detect anti-insulin antibody binding to the plate bound insulin. Unfortunately, these standard ELISA assays could not detect the antibodies predictive or diagnostic of Type 1 diabetes.

While radioactive assay methods are available for detecting the presence of insulin autoantibody, such methods are often costly and time consuming. Moreover, even utilizing radioactive insulin, one of the major problems of currently available assays is unacceptable variation in specificity and sensitivity between laboratories. Thus, accurate detection of human insulin autoantibody that are associated with the development of Type 1A diabetes has proven problematic.

Therefore, there is a continuing need for a reliable method of detecting insulin autoantibody.

SUMMARY OF THE INVENTION

Some aspects of the invention provide methods and kits for detecting the presence of insulin autoantibody in a fluid sample of a subject. Unlike conventional methods, methods of the invention utilize proinsulin to detect the presence of insulin antibody. In some aspects, methods of the invention detect the presence of insulin autoantibody in a fluid sample by a sandwich assay that results in the formation of a first proinsulin-insulin autoantibody-second proinsulin complex, if the insulin autoantibody is present in the fluid sample.

One particular aspect of the invention provides a method for detecting the presence of an insulin autoantibody in a subject, said method comprising:

(i) contacting a fluid sample of the subject with one or more reagent mixtures comprising a proinsulin under conditions sufficient to form a first proinsulin-insulin autoantibody-second proinsulin complex when the insulin autoantibody is present in the fluid sample;

(ii) determining the presence of the first proinsulin-insulin autoantibody-second proinsulin complex, wherein the presence of the first proinsulin-insulin autoantibody-second proinsulin complex is an indication that insulin autoantibody is present in the subject.

In some embodiments, such a method further comprises the step of attaching the first proinsulin-insulin autoantibody-second proinsulin complex, if present, onto a solid substrate prior to said step of determining the presence of the first proinsulin-insulin autoantibody-second proinsulin complex.

The formation of first proinsulin-insulin autoantibody-second proinsulin complex can be carried out in a two or more different reactions or in a single reaction vessel. Thus, yet in other embodiments, said step of contacting the fluid sample of the subject with one or more reagent mixtures comprises either:

(A) (1) contacting the fluid sample of the subject with a first proinsulin under conditions sufficient to produce a first product, wherein the first product comprises a first proinsulin-insulin autoantibody complex when the insulin autoantibody is present in the fluid sample; and (2) contacting the first product with a second proinsulin under conditions sufficient to produce a second product, wherein the second product comprises the first proinsulin-insulin autoantibody-second proinsulin complex when the first proinsulin-insulin autoantibody complex is present in the first product; or (B) contacting the fluid sample of the subject with a reagent mixture comprising a first proinsulin and a second proinsulin under conditions sufficient to form the first proinsulin-insulin autoantibody-second proinsulin complex when the fluid sample comprises an insulin autoantibody.

Within these embodiments, one of the first proinsulin or the second proinsulin comprises a labeling molecule and the other comprises a tagging molecule. In some instances, the first proinsulin-insulin autoantibody-second proinsulin complex, if present, is attached to the solid substrate by formation of a complex between the tagging molecule and a capture molecule that is attached to the surface of the solid substrate.

The tagging molecule is typically a non-radioactive tagging molecule. Exemplary non-radioactive tagging molecules include, but are not limited to, biotin, a carbohydrate, an immunoglobulin sequence, or a combination thereof.

The capture molecule is selected such that it has a selective affinity for the tagging molecule such that it can form a relatively tight complex. Exemplary capture molecules include, but are not limited to, streptavidin, lectin, protein A/G, an aptamer to proinsulin, or a combination thereof. As will be appreciated, typically the capture molecule is complementary complex forming molecule to the tagging molecule.

In one particular embodiments, the tagging molecule comprises biotin and the capture molecule comprises streptavidin.

In some embodiments of the invention, the first proinsulin is bound to the solid substrate surface. In this manner, when the fluid sample is contacted with the first proinsulin under appropriate conditions, a solid surface bound first proinsulin-insulin autoantibody is formed, if insulin autoantibody is present in the fluid sample.

Yet in other embodiments, the labeling molecule comprises a SULFO-TAG®, luciferase, sulfatase, phosphatase, peroxidase, a chemegeric compound, a fluorogenic compound, a nucleotide sequence, or a combination thereof. Typically, the labeling molecule allows detection of the first proinsulin-insulin autoantibody-second proinsulin complex by a non-radioactive detection method. Suitable non-radioactive detection methods include, but not limited to, fluorescence, electrochemical luminescence, phosphorescence, hybridization, or a combination thereof.

Other aspects of the invention provide methods for determining susceptibility of a subject to developing Type 1 diabetes or whether the subject has Type 1 diabetes using the methods described herein. Thus in some embodiments, one can determine susceptibility of a subject to developing Type 1 diabetes or whether the subject has Type 1 diabetes by using a method comprising:
  (i) contacting a fluid sample of the subject with one or more reagent mixtures comprising a proinsulin under conditions sufficient to form a first proinsulin-insulin autoantibody-second proinsulin complex when the insulin autoantibody is present in the fluid sample;
  (ii) determining the presence of the first proinsulin-insulin autoantibody-second proinsulin complex,
wherein the presence of the first proinsulin-insulin autoantibody-second proinsulin complex is an indication that the subject is susceptible to developing Type 1 diabetes or the subject has Type 1 diabetes.

Methods described herein are generally capable of detecting the insulin autoantibody at a concentration of about 100 pM or higher, typically at a concentration of about 10 pM or higher, and often at a concentration of about 1 pM or higher.

Still other aspects of the invention provide kits for detecting the presence of an insulin autoantibody in a fluid sample of a subject. Such kit typically include:
  (a) a solid substrate comprising a surface bound first proinsulin that is capable of producing a solid substrate bound proinsulin-insulin autoantibody complex when the solid substrate is contacted with the fluid sample comprising an insulin autoantibody; and
  (b) a reagent comprising a second proinsulin that is capable of producing a first proinsulin-insulin autoantibody-second proinsulin complex when the first proinsulin-insulin autoantibody complex is present.

Typically, kits of the invention provide a non-radioactive method for detecting the presence of insulin autoantibody.

The solid substrate can include a plurality of defined regions of surface bound first proinsulin. This allows one to simultaneously assay a plurality of samples. The solid substrate can include a material comprising a silicon wafer, glass, a metal, a plastic, a ceramic, a metal alloy, a polymer, or a combination thereof.

In some particular embodiments, the first proinsulin in the kits of the invention is bound to the surface of said solid substrate by a biotin-streptavidin complex.

Yet in other embodiments, the second proinsulin comprises a SULFO-TAG® labeling molecule.

Still in other aspects, methods of the invention utilize a first proinsulin molecules that is tagged and is attached to a solid phase and the second proinsulin molecule that comprises a detectable label. Unlike other conventional methods, methods of the invention utilize proinsulin rather than insulin to detect insulin autoantibody. The tags and labels are typically selected such that they do not significantly interfere with the binding of insulin autoantibody to proinsulin. In some embodiments, methods for detecting insulin autoantibody include:
  contacting the fluid sample of the subject with a solid substrate comprising a surface bound first proinsulin under conditions sufficient to produce a solid substrate bound insulin autoantibody-proinsulin complex when the insulin autoantibody is present in the fluid sample;
  contacting the resulting solid substrate of with a second proinsulin under conditions sufficient to produce a sandwiched insulin autoantibody complex when the insulin autoantibody-proinsulin complex is produced in the above step; and
  analyzing the resulting solid substrate of to determine the presence of insulin autoantibody in the fluid sample of the subject.

In some particular embodiments, methods include:
  (i) either incubating in a fluid phase both the first proinsulin and the second proinsulin (where one is tagged and the other is labeled) together with a fluid sample (e.g., blood, blood serum, etc. or any other fluid sample that may contain insulin autoantibody) with subsequent capture of the complex on a solid substrate through the tagged proinsulin, when the insulin autoantibody is present in the fluid sample or
  (ii) (a) contacting a fluid sample with a first proinsulin bound to a solid phase to produce a first proinsulin-insulin autoantibody complex when an insulin autoantibody is present in the fluid sample, and then contacting with a second proinsulin under conditions sufficient to produce a first proinsulin-insulin autoantibody-second proinsulin complex when the insulin autoantibody is present in the fluid sample; and
    (b) analyzing the resulting solid substrate to determine the presence of the first proinsulin-insulin autoantibody-second proinsulin complex, wherein the presence of the first proinsulin-insulin autoantibody-second proinsulin complex is an indication that the insulin autoantibody is present in the subject.

In some embodiments, analysis comprises detecting the signal produced by the first proinsulin-insulin autoantibody-second proinsulin complex. It should be appreciated that unless stated otherwise methods of the invention include detecting the signal produced by labeled proinsulin in the first proinsulin-insulin autoantibody-second proinsulin complex.

Typically, methods of the invention are directed to a non-radioactive methods for detecting insulin autoantibody, but radioactive labeling of the second proinsulin can also be employed. In some embodiments, the labeled proinsulin comprises a non-radioactive label covalently linked to proinsulin such as MSD Sulfo-Tag®, luciferase, europium or other fluorescent molecule, which upon covalent attachment to proinsulin does not interfere significantly with the binding of insulin autoantibody. In some instances a tag bound to a proinsulin is used to capture the complex to the solid substrate, e.g., a plate. Suitable tags include, but are not limited to, biotin (e.g., captured by streptavidin). It should be appreciated that other ligand pair that does not significantly compete with binding of insulin autoantibody to proinsulin can also be used. Depending on the label, the presence of the complex comprising a labeled proinsulin can be detected by electrochemical emission of light (e.g., using MSD Sulfo-Tag®), emission of light following catalysis (e.g., using luciferase), detection of radioactivity (e.g., using a radioactively labeled proinsulin), fluorescence including time resolved fluorescence (e.g., using Sm, Eu, Tb, and Dy ions).

Exemplary of tags that can be used to attach to a solid substrate include, biotin, multiple different protein affinity reagent pairs (e.g., pair carbohydrate-lectins, immunoglobulin sequence-protein A/G, aptamers to proinsulin, etc.) or a combination thereof.

In some instances, the solid substrate comprises a surface bound streptavidin, lectin, protein A/G, an aptamer to proinsulin, or a combination thereof.

In one particular embodiment, the tag comprises biotin.

Yet in another particular embodiment, the first proinsulin is bound to the solid substrate surface by biotin-streptavidin complex.

Still in other embodiments, the second proinsulin comprises a non-radioactive label that can be detected using a non-radioactive detection method.

In other embodiments, the label comprises Sulfo-Tag®, luciferase, sulfatase, phosphatase, peroxidase, chemegeric compounds, fluorogenic compounds, a primer suitable for PCR (e.g., a nucleotide having a suitable sequence for a real-time PCR), or a combination thereof.

Yet still in other embodiments, a radioactively labeled proinsulin can be used thereby.

Other aspects of the invention provide methods for determining susceptibility of a subject to developing Type 1 diabetes or whether the subject has Type 1A or autoimmune diabetes. Such methods include detecting the presence of insulin autoantibody in the subject using proinsulin molecules as described herein and detecting the presence of insulin antibody using the signal generated by the proinsulin label as discussed herein.

In some embodiments, methods of the invention are capable of detecting the presence of insulin autoantibody at a concentration of about 50 µU (microunits) or more, typically 40 µU or more, and often 30 µU or more of insulin autoantibody per mL of the fluid sample of the subject.

BRIEF DESCRIPTION OF THE DRAWINGS

FIG. 1 shows that both modified molecules were able to compete with $I^{125}$-insulin for binding to patients' insulin autoantibody.

DETAILED DESCRIPTION OF THE INVENTION

Figure 1:
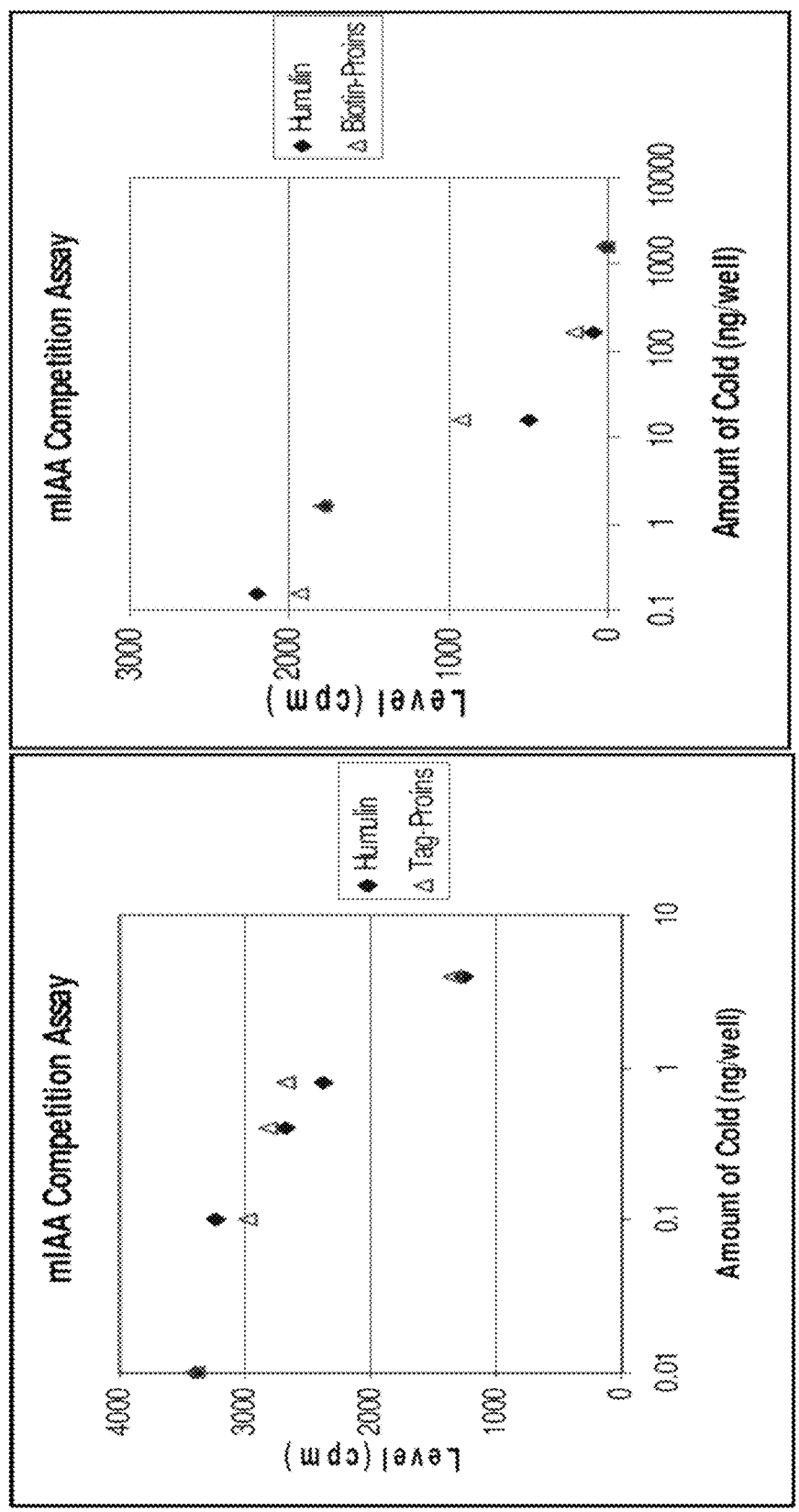
FIG. 1 is graph showing the result of biotinylated and Sulfo-Tag® labeled proinsulin as competitors in a fluid phase insulin autoantibody radioassay.

To date the detection of human insulin autoantibody that is highly associated with the development of Type 1A diabetes with assays not employing radioactive insulin has proven problematic. Thus in the Immunology of Diabetes Workshops no ELISA assay for insulin autoantibody has been validated and even for multiple assays utilizing radioactive insulin, unacceptable variation in specificity and sensitivity between laboratories has remained a major problem. The present inventors have overcome these shortcomings in detecting Type 1A diabetes associated insulin autoantibody by utilizing proinsulin as target autoantigen. In some instances, the proinsulin is covalently attached to a solid substrate. Thus, in some aspects of the invention, methods of the invention can detect insulin autoantibody with a plate based non-radioactive assay utilizing biotinylated proinsulin as bait and Sulfo-Tag® labeled proinsulin for detection. Sulfo-Tag® label is available from MSD (Gaitherburg, Md.) and its use as a label is described in MSD's website (see http://www.mesoscale.com). Other methods of the invention provide capturing exposed relevant insulin epitopes for a plate insulin autoantibody assay. Moreover, some aspects of the invention provide multiple assay formats that can be used to diagnosis and to predict the presence or the susceptibility of developing Type 1A diabetes in a subject. Still other aspects of the invention provide kits that are useful in detecting the presence of insulin autoantibody in a fluid sample of a subject. Such kits can be used to diagnose or determine the susceptibility or the presence of Type 1 diabetes in a subject.

Early studies indicated that the epitopes recognized by the insulin autoantibody that predicted the development of Type 1A diabetes were of high affinity and recognized unique conformational epitopes of the insulin molecule that were likely not available after binding of insulin directly to plates. The present inventors have found that the insulin autoantibody of the spontaneous animal model, e.g., the NOD mouse, can readily be detected in an ELISA format. In some instances, the present inventors have used a time resolved fluorescence detection methodology with plate bound insulin as target and competition with fluid phase insulin to enhance specificity. This difference between the detection of murine anti-insulin autoantibody and the human autoantibody in ELISA format despite equivalent signals with identical fluid phase radioassays (utilizing human insulin for both) was quite striking and reinforced the present inventors' belief that plate bound insulin obscured a critical epitope seen by most prediabetic patients.

In terms of the need for improved insulin autoantibody assays, in addition to the inability to develop ELISA format assays for insulin autoantibody the current fluid phase insulin autoantibody radioassays have proven difficult for many laboratories to implement. Though insulin autoantibody is usually of high affinity, capacities are very low and signals for the majority of patients are very low with radioassays (positives are usually set above the 99th percentile of normal controls). IDS workshops have demonstrated for the majority of laboratories consistent results for GAD, IA-2 and ZnT8 autoantibody; unfortunately, this has not been possible to achieve for insulin autoantibody. Therefore, the present inventors have sought improved insulin autoantibody assays. Since insulin consists of a relatively small protein of only 51 amino acids with an A and B chain, it is not surprising that plate bound insulin or biotinylated insulin through avidin do not allow detection of autoantibody.

Some aspects of the invention are based on the discovery by the present inventors that insulin autoantibody reacts with proinsulin (e.g., biotinylated proinsulin and Sulfo-Tag® labeled proinsulin) in fluid phase radioassays and in format for solid phase capture with specific ligand pair (e.g., Biotin and streptavidin). Based on this discovery, the present inventors produced biotinylated and Sulfo-Tag® labeled proinsulin and developed a solid substrate (e.g., plate) capture insulin autoantibody assay. Surprisingly and unexpected, it was discovered by the present inventors that streptavidin, but not avidin, was able to capture the biotinylated insulin with autoantibody bound proinsulin pairs (biotinylated and Sulfo-Tag® labeled) allowing the development of a plate capture highly reproducible non-radioactive assay for insulin autoantibody.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Subjects

Serum samples from 83 newly diagnosed patients with diabetes at Barbara Davis Center for Childhood Diabetes were selected for this study including samples positive for insulin autoantibody by radioassay at different levels or positive for one or more of other autoantibody to GAD65, IA-2, and ZnT8. The blood samples from these patients were collected within two weeks of diabetes diagnosis to exclude any possibility of induced insulin antibodies by exogenous insulin usage. Ninety-five age-matched normal control samples from general population were included in this study. Signed written consent forms were obtained from these participants.

Sulfo-Tag® Labeling of Proinsulin

Proinsulin (Eli Lilly) in 2×PBS was mixed with Sulfo-Tag® (MSD) at 1:5 molar ratio and incubated at room temperature for 2 hours in the dark. After incubation, the product was washed 6 times with PBS in a micro-centracon 3 (Millipore) to remove unbound Sulfo-Tag®. The final product was determined for protein concentration with a BCA kit (Sigma) and Sulfo-Tag® was determined by Spectrodometry at the wavelength of 450 nm.

Biotin Labeling of Proinsulin

The labeling was performed with a biotinylation kit (Pierce Biotech). Briefly, proinsulin (Eli Lilly) in 2×PBS was mixed with biotin (from the kit) at 1:5 molar ratio and incubated at room temperature for 1 hour. After incubation, the free biotin was removed with a desalting column provided in the kit. The protein concentration was determined with a BCA kit (Sigma) and biotin concentration by Spectrodometry at the wave length of 500 nm.

Insulin Autoantibody Plate Capture Assay

Suitable conditions for the assay were tested in a serial of experiments including at various concentration of Sulfo-Tag® labeled proinsulin and biotin labeled proinsulin, the serum volume, and serum dilution.

The Sulfo-Tag® at final concentration of 100 ng/ml and biotin labeled proinsulin at final concentration of 50 ng/ml were mixed with 50 µl of serum at serum dilution of 1:1 and incubated at room temperature for 2 hours followed by incubation at 4° C. for overnight (>16 hours). At the same day, the 96-well streptavidin coated MSD plate was blocked with 150 µl of 3% Blocker A (MSD) per well for overnight at 4° C. The next day, the blocked MSD plate was washed with PBST (1× PBS with 0.05% Twen-20) for 3 times followed by transferring overnight incubate into the MSD plate and incubating the plate at room temperature for 1 hour. Then the plate was washed again with PBST for 3 times to remove uncaptured Sulfo-Tag® proinsulin. Finally, 150 µl/well of 2× Read buffer (MSD) were added and the plate was counted on a MSD Sector Imager 2400.

Results

A number of Sulfo-Tag® labeled fluid phase assays have been developed that depend on complexing a biotinylated "bait" molecule with a Sulfo-Tag® labeled protein through binding of the analyte to both the biotinylated and Sulfo-Tag® labeled molecules. The biotin allows capture on solid phase while the Sulfo-Tag® provides light emission for detection of the captured complex using an MSD instrument. The present inventors have tested both biotinylated and Sulfo-Tag® labeled proinsulin as competitors in a fluid phase insulin autoantibody radioassay and demonstrated that both modified molecules were able to compete with $I^{125}$-insulin for binding to patients' insulin autoantibody. See FIG. 1.

Figure 2:
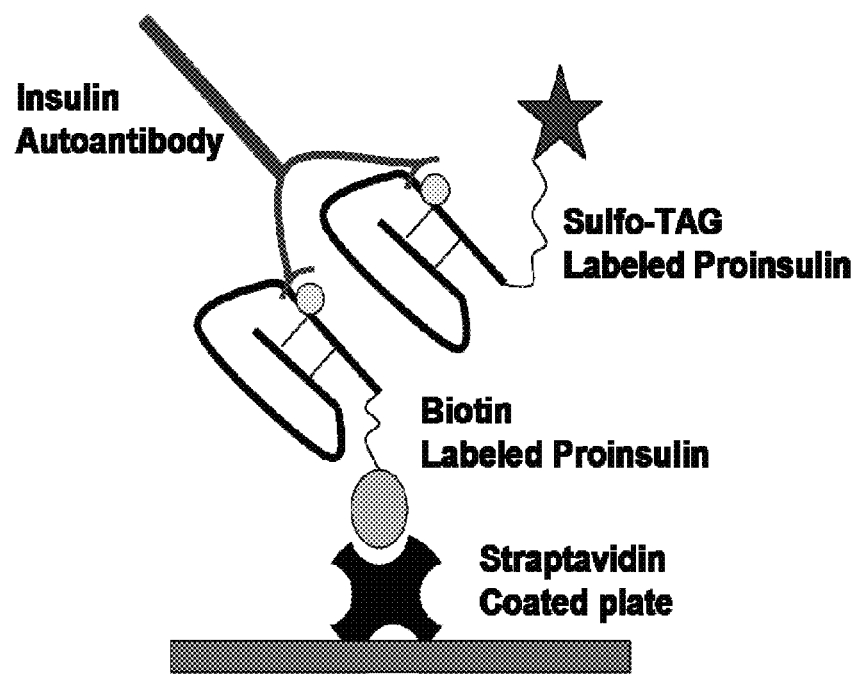
FIG. 2 is a schematic illustration of one particular embodiment of the present invention showing formation of a sandwich complex of insulin autoantibody (IAA) and a Sulfo-Tag® proinsulin and a biotinylated proinsulin.

With tagged proinsulin the amounts and ratios of biotinylated proinsulin and Sulfo-Tag® labeled proinsulin were tested in the presence of insulin autoantibody sera and control sera to maximize assay sensitivity. The proinsulin molecules were incubated with human sera and then added to streptavidin capture plates, and the plates were washed to remove non-bound Sulfo-Tag® labeled proinsulin. If autoantibody is present, it will link the Sulfo-Tag® labeled proinsulin to the biotinylated proinsulin which will be captured on the solid phase of the streptavidin coated plate as illustrated in FIG. 2.

Figure 3:
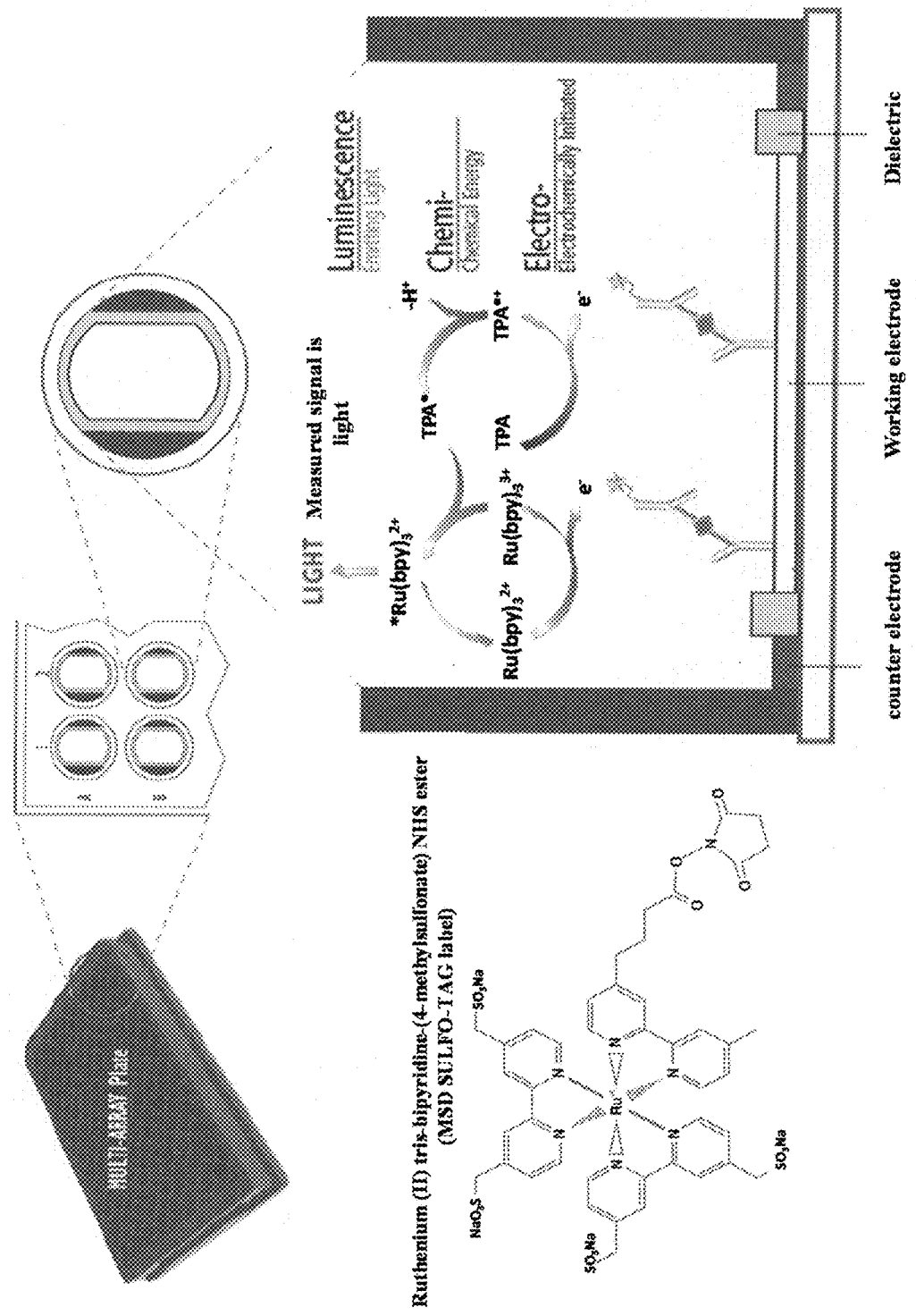
FIG. 3 is a schematic illustration showing a multi array assay kit for detecting insulin autoantibody. In this illustration, the amount and ratio of the biotinylated proinsulin and Sulfo-Tag® labeled insulin are directly related to the strength of signal generated.

After washing, detection of Sulfo-Tag® labeled proinsulin was accomplished with electrochemiluminescence. As illustrated in FIG. 3, the amounts and ratios of the biotinylated proinsulin and Sulfo-Tag® labeled proinsulin directly related to the strength of signal generated.

Figure 4:
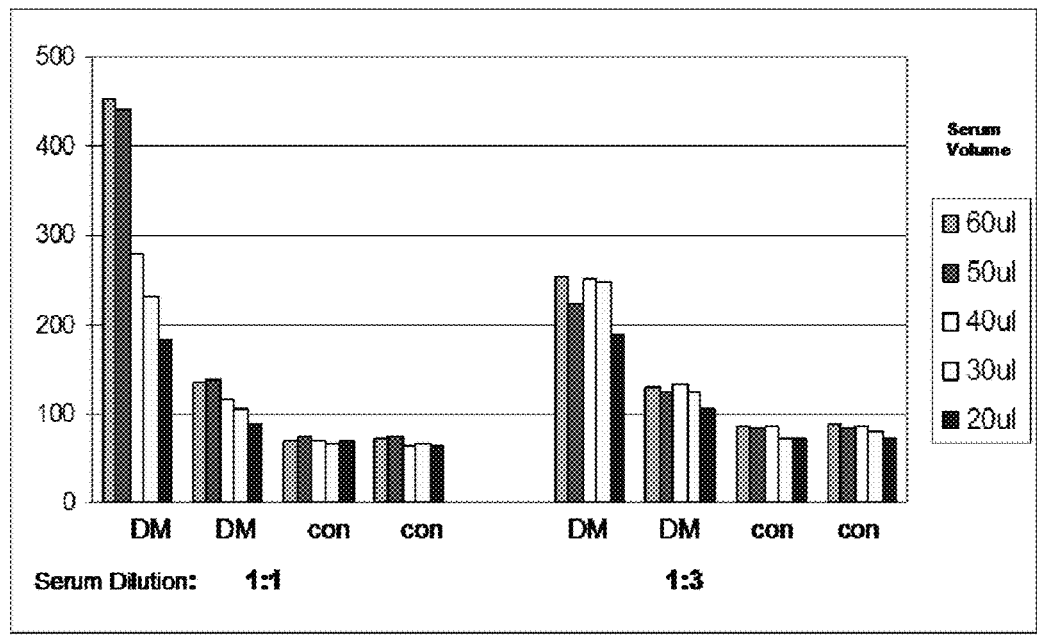
FIG. 4 is a graph showing a dose response of both low and higher titer insulin autoantibody positive sera at different dilutions.

For further experiments, the concentrations of the Sulfo-Tag® labeled proinsulin (100 ng/ml) and the biotinylated proinsulin (50 ng/ml) at a ratio of 2:1 were used. Using this concentration a dose response of both low and higher titer insulin autoantibody positive sera indicated that a volume of 50 µl of sera and the serum dilution at 1:1 allowed detection of all of the tested insulin autoantibody sera positive with fluid phase radioassay and that 50 µl of sera gave a stronger signal compared to a lesser amount of sera. See FIG. 4.

Figure 5:
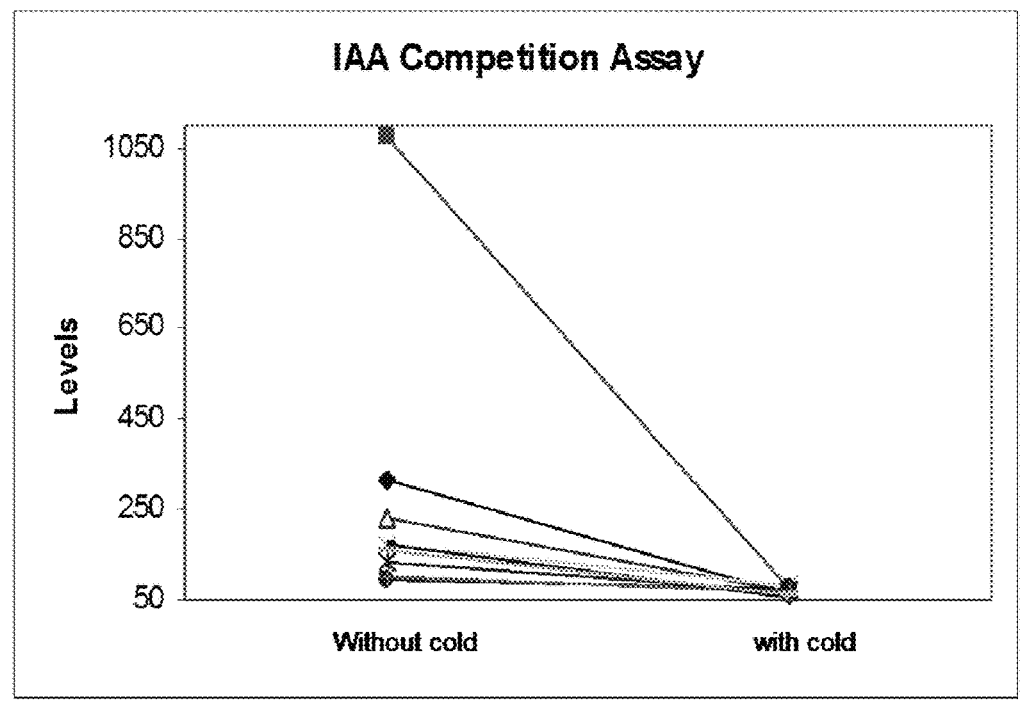
FIG. 5 is a graph showing the results of IAA competition assay at different levels of IAA signals demonstrating specific inhibition by insulin. The graph shows that substantially the entire specific signal was abrogated with cold insulin competition and there was no significant evidence for proinsulin specific autoantibody in the samples tested.

Competition test with unlabeled insulin for 9 patient serum samples at different levels of IAA signals with this new assay demonstrated specific inhibition by insulin. The results showed that substantially the entire specific signal was abrogated with cold insulin competition and there was no noticeable evidence for proinsulin specific autoantibody in the samples tested. See FIG. 5.

Figure 6:
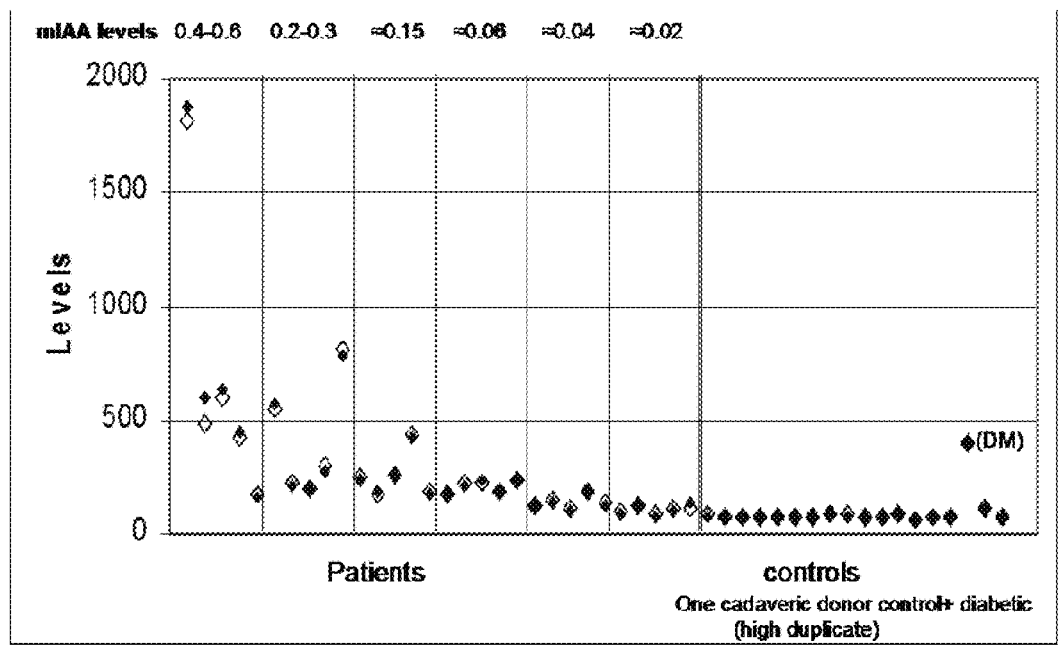
FIG. 6 is a graph showing the result of IAA plate capture assay of patients with varying levels of insulin autoantibody and a series of control samples.

A larger set of samples was evaluated to test the reproducibility of the assay with duplicate determinations plotted for patients with varying levels of insulin autoantibody and a series of control samples. All but one of the patient samples exceeded the control samples with one control (a diabetic) having a high level of antibody to insulin. See FIG. 6.

Figure 7:
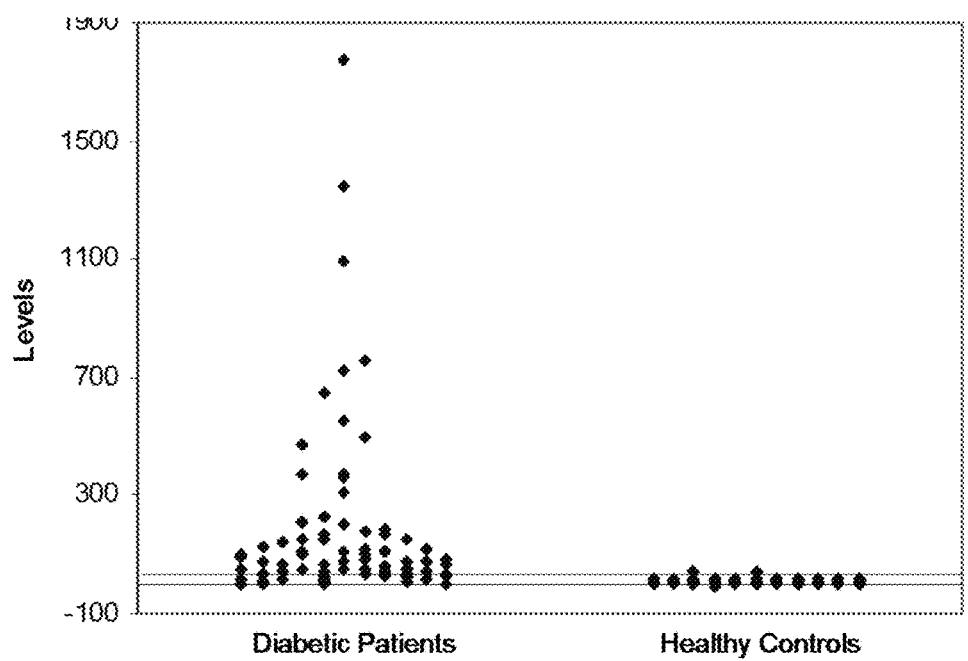
FIG. 7 is a graph showing the result of plate capture IAA assay for randomly selected 83 newly diagnosed patients with diabetes who were either mIAA positive or other autoantibody positive (GAD65, IA-2, or ZnT8) and 95 age-matched normal control subjects.

Randomly selected 83 newly diagnosed patients with diabetes who were either mIAA positive or other autoantibody positive (GAD65, IA-2, or ZnT8) and 95 age-matched normal control subjects were tested. Using a cutoff of 98% of specificity among 95 healthy control, 66/83 (80%) diabetic patient were positive for this new assay. The results for all patients and controls are shown in the FIG. 7.

Figure 8:
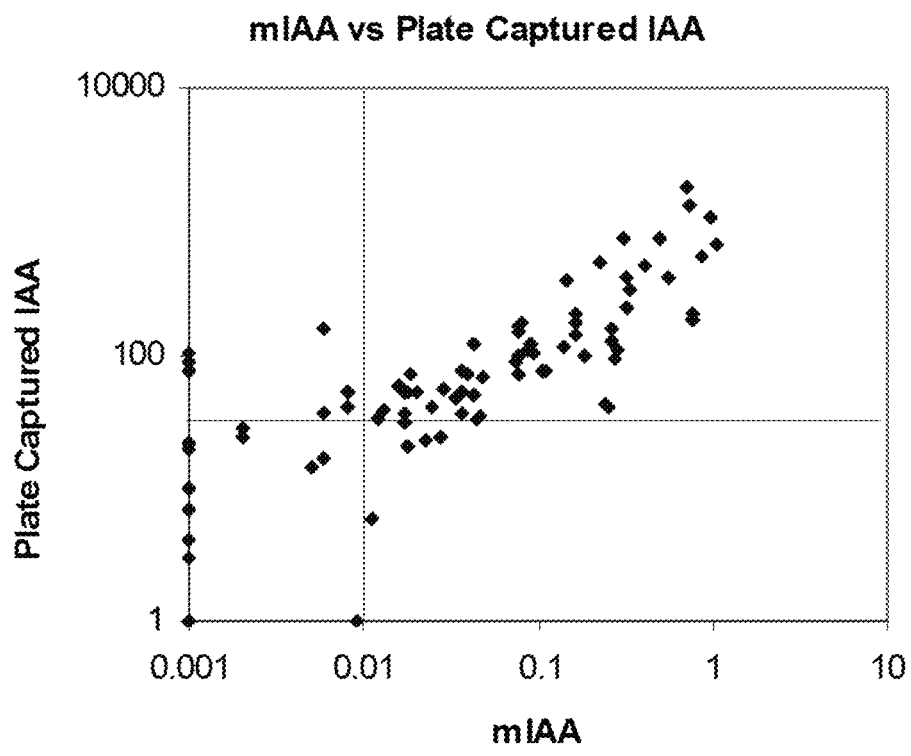
FIG. 8 is a comparison graph between mIAA radioassay and the plate capture IAA assay.

Compared with mIAA radioassay among these 83 diabetic patients, the levels were in general well correlated ($R^2$=0.5929). There were 54 samples shown positive in both assays and the plate capture IAA assay gained 7 positives and lost 4 at the low level positive samples. The correlation of two assays is shown in FIG. 8.

Discussion

In 1974 Bottazzo and Donniach reported the presence of autoantibody in sera of patients with diabetes and polyendocrine autoimmunity, ushering in the cytoplasmic islet cell autoantibody assay that utilized frozen sections of human pancreas. Though this assay is still utilized, it has been largely replaced by the measurement of autoantibody reacting with defined islet autoantigens and in particular insulin, GAD65, IA-2, and ZnT84, 15-17. Large prospective studies have documented that the presence of >=2 of these autoantibody is highly predictive of progression to Type 1 diabetes. The presence of single autoantibody confers a much lower risk for relatives of patients with Type 1 diabetes to become diabetic. Given that Type 1A diabetes has a prevalence of approximately 1/300, highly specific assays are of importance and many of the autoantibody assays for islet autoimmunity are set to call "positive" for signals greater than the 99th percentile of normal controls. The least reproducible of the biochemical assays for islet autoantibody in multiple workshops over the past two decades has been the assay for insulin autoantibody and improved versions of this assay are needed to allow international standardization. This is a particularly important assay in that insulin autoantibody is often the first autoantibody to appear. When it first appears, insulin autoantibody is already of high affinity. Presence of insulin autoantibody is age related (log-linear inverse relationship). Almost all children developing Type 1A diabetes prior to age five express insulin autoantibody, while children developing after age 12 and adults seldom express insulin autoantibody.

Despite the importance of insulin autoantibody in predicting Type 1A diabetes, currently no adequate (validated in CDC sponsored IDS workshops) non-radioactive assay is available for detecting insulin autoantibody. The present invention overcomes the fundamental difficulty of developing a solid phase capture non-radioactive insulin autoantibody assay by utilizing tagged (e.g., biotinylated) proinsulin and a capturing agent (e.g., streptavidin) bound to a solid support. Methods of the invention result in very reproducible signal with ability to detect even a low concentration of insulin autoantibody similar to those detected by the radioassays. The Sulfo-Tag® detection system provides for extremely high throughput and high sensitivity of detection of bound antigen and a very convenient assay methodology and rapid counting.

Some methods of the invention provide a rapid solid phase capture assay that can be adapted to many different islet autoantigens including insulin. Other aspects of the invention provide methods for screening or testing a large number of samples simultaneously.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of detecting whether an insulin autoantibody is present in a fluid sample of a subject, wherein the fluid sample comprises blood, serum, or plasma, the method comprising:
    (i) contacting the fluid sample of the subject with a first proinsulin and a second proinsulin under conditions, whereby a first proinsulin-insulin autoantibody-second proinsulin complex is formed when the insulin autoantibody is present in the fluid sample, thereby forming a first system,
        wherein the second proinsulin comprises proinsulin labeled with an electrochemical luminescence (ECL) labeling molecule, wherein the ECL labeling molecule comprises a ruthenium (II) tris-bipyridine-(4-methylsulfonate) group, and
        wherein the first proinsulin comprises proinsulin labeled with a biotin tagging molecule;
    (ii) contacting the first system formed in step (i) with a solid substrate comprising a surface-bound capture molecule which is bound to the surface of the solid substrate, wherein the surface-bound capture molecule comprises streptavidin,
        whereby, if the first proinsulin-insulin autoantibody-second proinsulin complex is present in the first system, the biotin tagging molecule binds to the streptavidin on the surface of the solid substrate, thereby attaching the first proinsulin-insulin autoantibody-second proinsulin complex to the solid substrate; and
    (iii) determining whether a first proinsulin-insulin autoantibody-second proinsulin complex is attached to the solid substrate, wherein the presence of the first proinsulin-insulin autoantibody-second proinsulin complex attached to the solid substrate indicates that insulin autoantibody is present in the fluid sample of the subject.

2. The method of claim 1, further comprising removing any unbound first proinsulin from the surface of the solid substrate prior to step (iii).

* * * * *